United States Patent [19]

Lindenmeier et al.

[11] Patent Number: 5,846,236
[45] Date of Patent: Dec. 8, 1998

[54] HIGH FREQUENCY-SURGICAL GENERATOR FOR ADJUSTED CUTTING AND COAGULATION

[75] Inventors: Heinz Lindenmeier, Planegg; Georg Lohr, Ottobrunn; Karl Fastenmeier, Munich; Gerhard Flachenecker, deceased, late of Ottobrunn; Hildegard Flachenecker, legal representative, Ottobrunn, all of Germany

[73] Assignee: Karl Storz GmbH & Co., Tuttlingen, Germany

[21] Appl. No.: 674,196

[22] Filed: Jul. 1, 1996

Related U.S. Application Data

[63] Continuation of Ser. No. 193,110, Jul. 18, 1994, abandoned.

[51] Int. Cl.$^6$ .................................................... A61B 17/39
[52] U.S. Cl. ................................................................ 606/38
[58] Field of Search ........................................ 606/37, 38

[56] References Cited

FOREIGN PATENT DOCUMENTS 3530335   3/1987   Germany .

Primary Examiner—Lee Cohen
Attorney, Agent, or Firm—Donald D. Mon; David O'Reilly

[57] ABSTRACT

The present invention relates to a high-frequency surgical generator (1) for adjusted cutting and coagluation having adjustment devices for setting the momentary electric output values, such as, e.g., current, voltage and power and having a device for direct and/or indirect determination of the state of the tissue in the vicinity of the cutting electrode. The present invention is distinguished by a time-interval transmitter and electronic desired-value transmitters being provided and one mode of operation of at least two different modes of operation having different operative purposes being selected in successive time intervals and an electronic memory having evaluation electronics, to which the output value of the measurement device is transmitted and the output signal of the evaluation electronics is transmitted to the electronic desired-value transmitters in conjunction with the output value of the measurement device with the aid of which the temporal course of the electric output values of the high-frequency generator for the selected mode of operation are suitably set.

16 Claims, 4 Drawing Sheets

HIGH FREQUENCY-SURGICAL GENERATOR FOR ADJUSTED CUTTING AND COAGULATION

This is a continuation of application Ser. No. 08/193,110 filed on Jul. 18, 1994, now abandoned.

TECHNICAL FIELD

The present invention relates to a high-frequency generator for high-frequency surgery.

STATE OF THE ART

High-frequency currents are employed in surgery to remove tissue if the site of the operation can be reached through the natural body openings, but a scalpel cannot be used without opening the body of the patient. For example, in urology tumors in the bladder or excrescences of the prostate gland can be removed using transurethally entered surgical instruments with the aid of high-frequency currents. In a similar manner in enterology, e.g., polyps can be removed from the walls of the intestines. The cutting electrode of the surgical instrument only cuts as long as the generator supplying the high-frequency current is activated, thereby ensuring safe entry and removal of surgical instruments through the natural openings of the patient's body.

Moreover, high-frequency currents are employed in surgery for bloodless cutting and to stop bleeding. There are state-of-the-art high-frequency generators equipped with a so-called "cutting mode" as well as a "coagulating mode". These generators are suited for separating tissue and for pinpoint stoppage of bleeding, coagulating. They are primarily used in endoscopic surgery, such as e.g., in urology, gynecology, polypectomy, etc. In addition to this, there are high-frequency generators that have only a coagulating mode. These so-called coagulators are employed in open-body surgery in order to close profusely bleeding severed vessels or to stop large-surface, diffuse hemorrhaging.

One problem in high-frequency surgery is the correct dosage of the momentarily applied high-frequency power. The minimum required high-frequency power for good cutting can fluctuate severely. It depends on the consistency of the tissue, the conductivity and the water content of the tissue, the shape and size of the electrodes, the cutting depth and speed, and other electric parameters subject to certain, in many cases, very abruptly occurring changes in the course of an operation. The usual high-frequency setting arrived at through experience, therefore, results in, on average, clearly too great a high-frequency power to the risks of which the surgeon has to consciously expose his patient and himself. In order to be able to keep these risks to a minimum, respectively to be able to almost exclude them, the momentary output power of the high-frequency generator would have to be controlled automatically in such a manner that it corresponds at all times to the minimum absolutely necessary.

An increase in the input power results in higher coagulation of the tissue at the surface of the incision permitting in this way to stop the bleeding. This is not necessarily required in surgery in which there is not much bleeding anyway. Also in the case of surgical techniques in which a large volume of tissue is removed, such as, e.g. in urology, cut-surface coagulation is not necessarily required during the cutting, because subsequent cutting is into lower-lying layers of tissue. Small, defined coagulation is, however, often desired in order to avoid unnecessary bleeding and a clear view of the site of the operation is maintained. In other types of operations, such as polypectomy, in which the entire surgery optimally consists of a single incision, optimum coagulation is, however, already mandatory during the incision.

A continuous high-frequency current is employed when cutting with high-frequency currents. In high-frequency coagulation, the Joule effect heat of the high-frequency current is utilized to stop the bleeding. For this purpose, a high-frequency current from a coagulation probe is passed over to the surface of the hemorrhage. The source of the hemorrhage can be a severed vessel, usually an artery, or large surface hemorrhaging in the form of bleeding from many little, severed capillaries. There are two processes which can be differential in coagulation. Low-voltage coagulation usually utilizes a continuous high-frequency current selected to be so low that a cutting effect of the probe cannot occur. On the other hand, for high-voltage coagulation, only pulsed high-frequency currents are employed. In this event, the average power input is so small that a cutting effect of the probe cannot occur. On the other hand, the voltages are so high that an insulating layer on the probe, that can result from accumulated contamination, is penetrated by a spark. Coagulation with voltage pulses can, therefore, also be carried out if it cannot be ensured that the probe is clean metal during coagulation.

An apparatus for minimizing the power when cutting human tissue with high-frequency current is described in the German patent P 25 04 280. In this apparatus, the size and intensity of the electric arc between the cutting electrode and the tissue to be cut is determined with the aid of an indicator device and the electric signal derived therefrom is transmitted to an adjustment device. This adjustment device compares this signal with the desired-value program of a desired-value transmitter and derives therefrom a variable which sets the strength of the output current of the generator in such a manner that the intensity of the electric arc is in keeping with the desired-value program. It has, however, been shown that a constant electric-arc intensity is not simultaneously accompanied by constant coagulation results, i.e, stoppage of the bleeding of the cut surfaces. Apparently, the conditions for even cutting and good coagulation are so different that both processes cannot be optimally carried out with a single, common measure like a constant intensity arc. For this reason, the German patent P 25 04 280 provides a desired-value transmitter (i.e. reference generator) that adjusts the electric-arc intensity according to a desired program value in such a manner that time intervals in which a current strength required for cutting is set alternates with time intervals in which a high-frequency generator current strength required for coagulation is set. In order to draw up a reference program, however, it is necessary to have precise knowledge of the parameters to be expected during the operation, such as type of tissue, fluid content, blood-vessel density of the tissue, cutting speed, cutting depth, etc. In practice, setting up such a reference program is, therefore, frequently only partly feasible or not at all. Even in the event of minor deviations of the assumed parameters from the actual ones, the desired-value program can deviate to such a degree from the optimum that neither the cutting effect nor the coagulation effect are really optimum.

Such a reference program is also not flexible if a very large blood vessel was opened during an earlier cut and has not completely closed when by the reference program value as set. In this case, solely coagulation without any cutting effect has to be conducted in the following step. This is not possible with the described reference program, because time intervals with coagulating function alternate with time intervals with cutting function. According to the state-of-the-art, in this case only coagulation with a pulsed, uncontrolled coagulation current is possible. Moreover, cases of a too high or a too low generator setting can occur. In the event of too high a setting of the high-frequency generator power, an electric arc with all the described drawbacks occurs anew and simultaneously, of course, at this moment undesirable cutting effects can set in again. If the power setting of the high-frequency generator is too low, the coagulating effect is not sufficient and the bleeding cannot be adequately stopped.

As a solution to the problem, a generator is described in the German patent DE 35 15 622, which changes the output voltage of the generator with the aid of measurement devices, an adjustment device and an additional timer, in such a manner that three time periods having exactly prescribed output voltage conditions repeat in continuous succession.

Laboratory measurements have revealed that adequate surgery results may be obtained with this generator. This is especially the case if the tissue conditions are constant and the cutting electrode is moved through the tissue with a constant velocity. Practical utilization of such a process is conceivable in urology. In this case, the cutting loop is rigidly, mechanically attached to the actuating lever in such a manner that the loop can be moved at a defined, constant rate of speed. In this case, too, there is such a clear view of the operation area and all possible operation sites are easily accessible so that in the event of unsuccessful coagulation, the hemorrhaging site can be recoagulated.

In other surgical techniques, such as polypectomy in which the point of the surgery is very difficult to reach and there is no clear view of the operation area, recoagulation is hardly feasible. Wire loops guided by a long endoscope to the site of the operation are preferably used to remove polyps. Due to the mechanical design of these instruments, movement of the cutting loop at a defined rate of speed is not possible. Moreover, dosage of the pulse intensity can also only be rough due to the friction within the instrument. Laboratory tests with the above-mentioned generator and typical polypectomy loops have shown very poorly reproducible coagulating behavior. Thus very good coagulation may be obtained in some incisions, whereas in other incisions the tissue is cleanly cut in the briefest time without coagulation. This shortcoming occurs, in particular, if the cut is through an area having different types of tissue or if the cutting electrode has accummulated a crust of coagulated blood and clumps of tissue.

In coagulation it often happens that the probe adheres to the surface of the tissue. In this event, the tissue particles and coagulated proteins adhere firmly to the surface of the probe and glue it to the coagulating tissue. If the surgeon tries to tear the probe from the point of coagulation with force, a part of the coagulated tissue will also rip off. As a result the just coagulated hemorrhage may start bleeding again making further coagulation necessary. Moreover, a probe with the accummulated tissue on it makes any further coagulation difficult and has to be cleaned prior to the next coagulation. In endoscopic surgical techniques, such as in urology, this is connected with great amount of time and effort, because the surgical instrument has to be removed from the body.

In order to prevent tissue from sticking to the probe, coagulators employing a fluid or gaseous medium for transmitting energy are utilized, forming between the electrode and the tissue a conductive intermediate layer.

Devices employing an ionized beam of gas for coagulation are also known, described for example in: H. D. Reidenbach, Hochfrequenz- und Lasertechnik in der Medezin, Springer Verlag, 1983. In this case, however, supplying fluid or gas to the tip of the electrode in the device is technically very complex. As laboratory tests have shown, only superficial coagulation is possible with these devices. Deep coagulation and modern bipolar coagulation techniques cannot be carried out with these devices. Probes that touch the surface of the tissue are required for this purpose. It is not possible to use the same probe for cutting and coagulating.

DESCRIPTION OF THE INVENTION

The object of the present invention, therefore, is to create a high-frequency generator for high-frequency surgery ensuring, by adapting to the conditions at the operation area, rapid separation of tissue with minimum required power while simultaneously stopping hemorrhaging in a defined manner and permitting high-frequency coagulation in such a manner that following coagulation, the probe can be removed from the tissue without the risk of ripping off the coagulated layer.

The objective is achieved by the apparatus and methods disclosed in the appended claims. Further improvements of the present invention are set forth in the subclaims.

With the aid of a device for determining the state of the tissue near the cutting electrode, a high-frequency generator having adjustment device for providing the momentary electric output values is set by a desired-value transmitter (i.e. reference generator). For this purpose, a suitable mode of operation is selected from at least two different modes having different surgical goals with the aid of a timer in successive time intervals. The output of the high frequency generator over time is controlled by an electronic memory with analytic circuitry which receives the output of a tissue state measurement device. This system can maintain instantaneous optimum operational parameters by taking into consideration the actual conditions at the site of the operation and the course of the operation so far. For this purpose, the electronic desired-value transmitter (i.e. reference generator) evaluate the output values of the measurement devices and the output signal of the memory. Taking into consideration the actual conditions at the site of the operation and the hitherto temporal course of the operation, this system can set the momentarily required mode of operation with the optimum parameters of the mode of operation. For the technical realization of the system, it is advantageous to use mixed analog/digital technology or to carry out a part of the control functions with the aid of a microprocessor or a control computer.

An especially advantageous embodiment is that decision of logic decider automatically decides at the end of a time interval which mode of operation shall be selected in the succeeding interval. The decision is made on the basis of the output value of the electronic memory having evaluation electronics and the output value of the measurement device.

Another avantageous embodiment is that a switch-off element is provided that sets the duration of the succeeding time interval using the output values of the measurement device. In this way, upon achieving the desired surgical goal during the time interval, this time interval is terminated.

In order to determine the state of the tissue in the immediate vicinity of the cutting electrode it is useful to dispose a measurement device in the immediate vicinity of the cutting electrode.

As an alternative, the respective data can also be gained by an evaluation of the electric signals at the output of the generator. Likewise, a test signal, that is transmitted to the cutting electrode, can be generated with the aid of a test-signal generator. The state of the tissue in the vicinity of the cutting electrode can be determined with a test-signal measurement device. This test signal has in general so little power that it itself causes no thermal effects in the tissue. Therefore, it can be switched on even if the power generator is switched off.

An advantageous embodiment of the present invention consists of being able to select at least one mode of operation having surgical purpose of "cutting" and at least one mode of operation having the surgical purpose "coagulating". In the case of a typical incision into muscular tissue, a temporal sequence of cutting and coagulating modes of operation would set in. If, e.g., a blood vessel is severed, the mode of operation selector sets, upon need, several successive time intervals with coagulating modes of operation.

For coagulation itself, there are several processes. One that permits coagulating in greater depths of tissue, operates with generator voltages set so low that cutting is not yet possible. Such a mode of operation is referred to hereinafter as "low-voltage coagulation". Coagulation of the tissue surface even in tissue or bone crevices is possible with short high-voltage pulses. These pulses are selected so short that, in this case too, cutting in not possible.

Frequently the tissue has to cool off. It is, therefore, advantageous if the time intervals with negligibly low generator power can be selected. During those times, the plasma formed by the electric arc is also removed. Insulating vapor layers that might be present are also removed.

In a particularly advantageous embodiment of the generator, the measurement device has a device for determining the tissue impedance at the cutting electrode. The decision whether to coagulate or cut in the next time interval can be derived from the value of the tissue impedance. A low impedance indicates that there is no vapor layer between the cutting electrode and the tissue or that blood has even exuded and creates a conductive connection from the cutting electrode to the tissue. In this event, coagulating must occur in the next time interval. If the impedance is high, there is a vapor layer preventing condition, the tissue has coagulated and cutting can occur in the next interval.

In order to realize high-frequency coagulation, in which according to the object of the present invention the probe can be removed safely from the tissue without damaging the coagulated tissue, the high-frequency generator is, in accordance with the present invention, set temporally successively in different modes of operation. A first mode of operation (a) has a coagulating function, whereas a second mode of operation (b) has a cutting function. The modes of operation of the generator are set by the control unit; following activation of the generator, first the first mode of operation (a) having a coagulating function followed by the second mode of operation (b) having a cutting function.

Depending on the application, various processes may be employed for coagulation in the first mode of operation (a) having a coagulating function. Coagulation in greater tissue depth can be achieved by applying low voltages, because in this way the tissue can slowly be heated down into the deeper zones. For scabbing on the tissue surface, coagulation with short voltage pulses of high amplitude are useful. The high voltage causes an electric arc to the tissue to form and reaches points that have no ohmic contact to the coagulation electrode. Due to the high input energy, the surface of the tissue coagulates quickly and therefore becomes a high impedance, thereby preventing further current flow, further energy input and heating of low-lying tissue layers. In order to prevent a cutting effect due to the electric arc, the generator voltage is usually pulsed at an average power so low that cutting is impossible.

Monopolar or bipolar arrangements of electrodes can be employed for coagulation. In certain surgical techniques, such as in urology, the same instrument is used to cut and coagulate. Thus monopolar coagulation is useful. In open surgery, however, a separate coagulation electrode can be employed. In this case, bipolar coagulation is often more advantageous, because it results in a defined current flow and therefore in defined heat development and coagulation between the electrodes.

In the second mode of operation (b) having a cutting function, there are different processes available depending on the demands. What is important is to ensure that the electric arc required for cutting forms inspite of the coagulated surface of the tissue. This can be ensured by applying a sufficiently high voltage. If this voltage, however, is too high, the excess energy is transmitted into the patient. This can be avoided with an apparatus like the one described in the German patent 2504280. In this apparatus, the size and intensity of the electric arc between the cutting electrode and the tissue to be cut is determined with the aid of an indicator device, and the electric signal derived therefrom is transmitted to an adjustment device. This adjustment device compares this signal with the desired-value program of a desired-value transmitter and derives therefrom a variable value that sets the strength of the output current of the generator in such a manner that the intensity of the electric arc is in keeping with the desired-value program. In this way, only the energy needed for maintaining the electric arc required for cutting is delivered.

A control unit switches the generator following its activation first to a first mode of operation (a) having a coagulating function. After termination of the coagulation, which is determined by the surgeon or automatically by the generator, the control unit switches the generator briefly to the second mode of operation (b) having a cutting function. In this way, the cell residue gluing the electrode to the tissue surface is vaporized. Upon cutting, an electric arc, which always jumps to the cells lying closest to the electrode, forms at the electrode. These cells vaporize and a vapor layer forms between the electrode and the surface of the tissue. The electrode is, therefore, separated from the tissue and can be easily removed.

An especially advantageous embodiment is provision of a timer which gives a preset time for the time interval of "cutting". This time is measured in such a manner that there is sufficient time to form an electric arc between the electrode and the tissue. Yet, this time is too short for the electrode to significantly penetrate the tissue. In applications in which always the same type of tissue is coagulated, the required time can be determined by experimenting and set permanently.

In the case of applications in which different types of tissue are coagulated, a fixed, preset time may not suffice, under some circumstances, to always be able to remove the loop from the tissue. For this reason, in another embodiment, the apparatus for coagulating is expanded in such a manner that it possesses a measurement device having an evaluation unit. This measurement device measures the electric parameters at the generator output during the first mode of operation (a) having a coagulating function and determines therefrom the optimum duration of the next interval with the second mode of operation (b) having a cutting function.

Furthermore, a timer is provided which terminates the second mode of operation (b) according to a time given by the measurement device having an evaluation unit. The timer is set accordingly by the output signal of this measurement device having an evaluation unit. In order to measure the electric parameters at the operation site, the output values of the generator itself or the signal of an auxilliary generator can be utilized for measurement. By way of illustration, the tissue impedance can be determined during the first operation mode (a) and a time proportional to this impedance can be given for the second mode of operation (b), permitting in this manner a longer cutting period for heavily scabbed and, therefore, high-ohmic tissue surfaces and thus also better removal of the probe.

Another advantageous embodiment consists of an evaluation circuit being provided which determines commencement of cutting directly or indirectly. In the second mode of operation (b) during a cutting function, the evaluation circuit transmits a signal to the control unit in a manner that the time interval with the second mode of operation (b) is terminated at a preset time following determination of commencement of cutting. A cutting action for a brief period is enough in order to partially remove the probe from the tissue. This cutting, however, should be continued for a negligible period so that it is certain that the entire length of the probe separates from the tissue. This time must, however, be selected so short that the probe cannot significantly penetrate the tissue.

Another advantageous embodiment consists of the evaluation circuit containing a mechanical sensor which determines penetration of the tissue by the probe. Thus the distance of the probe from the surrounding tissue can be determined by means of a distance sensor. Optical sensors that permit contactless measurement of the distance are especially suited for this purpose.

Directly following commencement of cutting, the impedance between the probe and the tissue changes. As laboratory measurements revealed, in general, a distinct rise in this impedance can be measured when cutting commences. This occurs especially when cutting following a low-voltage coagulation. If, on the other hand, the tissue is a very high impedance following high-voltage coagulation, the impedance may drop at the commencement of cutting. In this event, the electric arc bridges the high impedance tissue layer. For this reason, an advantageous embodiment consists of the evaluation circuit containing a device for measuring and evaluating the impedance, in which the measurement signal is compared with a desired value in order to detect the change in impedance. Instead of the measurement signal, a combination of the measurement signal and one or several of its derivations can be used for evaluation.

Characteristic of cutting is the electric arc occurring with it. Commencement of cutting can, therefore, be determined from an evaluation of the spectral distribution frequency of the generator output signal. Therefore, an advantageous embodiment consists of an evaluation circuit having a device for evaluating the spectral fraction at the output of the generator. The generator signal itself or also the signal of an auxilliary generator or a combination of both signals can be used for the evaluation. The evaluation itself occurs by comparing the amplitudes of the spectral fractions generated by the generator, respectively the electric arc.

BRIEF DESCRIPTION OF THE DRAWINGS

The present invention is made more apparent, by way of example, without the intention of limiting the scope or spirit of the overall inventive concept in the following using preferred embodiments with reference to the drawing to which is explicitly referred for the disclosure of all inventive details not explained more closely herein. Shown is in.

DESCRIPTION OF A PREFERRED EMBODIMENT

Figure 1:
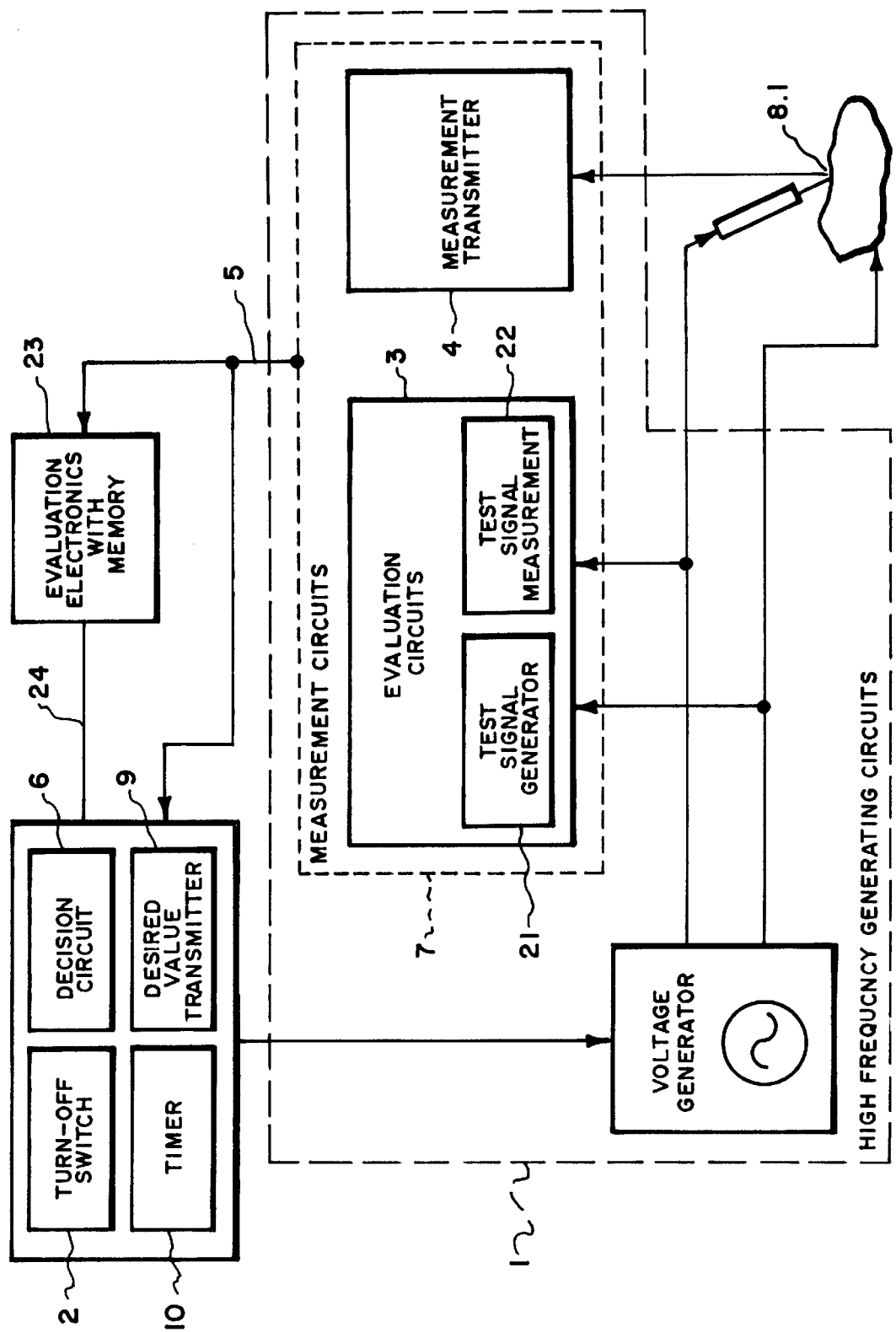
FIG. 1 A basic circuit diagram of an invented high-frequency surgical generator for coagulating cutting, FIG. 2 An exemplary representation of the generator output voltage in the course of three time intervals, FIG. 3 An exemplary representation of the generator output voltage for a coagulating incision having 4 different surgical purposes, FIG. 4 A basic circuit diagram of the major functions of the high-frequency surgical generator for carrying out the high-frequency coagulation.

FIG. 1 shows the basic circuit diagram of the high-frequency surgical generator according to the present invention. The high-frequency generator (1) for high-frequency surgery has adjustment devices for setting the momentary electric output values, such as, e.g., current, voltage and power as well as a tissue state measurement device (7) for direct and/or indirect determination (i.e. impedance) at the state of the tissue in the vicinity of the cutting electrode (8.1).

This apparatus contains a probe operations monitor and measurement transmitter (4) in the immediate vicinity of the cutting electrode. Moreover, it contains an evaluation unit (3) for evaluating the generator electric output voltage values. This unit contains a test-signal generator (21), the test signal of which is transmitted to the cutting electrode and is measured with the aid of the test-signal meter or measuring device (22), for selective direct or indirect determination of the state of the tissue in the vicinity of the cutting electrode. Furthermore, the apparatus contains evaluation electronics (23) with electronic memory to receive the output value (5) of the tissue state measurement device (7) for direct and/or indirect determination of the state of the tissue in the vicinity of the cutting electrode. The output value (24) of the electronic memory having an evaluation electronics and the output values (5) of the tissue state measurement device (7) are transmitted to turn-off switch (2), decision logic of decider (6), reference generator (9) and timer (10).

Turn-off switch (2) restricts the duration of the following time interval (13) using the output value of Tissue state measurement device (7), decision logic in decider (6) selects the mode of operation for the following time interval (13) at the end of the preceding time interval (12) automatically. The electronic reference generator (9) determines the temporal course of the electric output values of the high-frequency generator for the selected mode of operation. Timer (10) determines and fixes the duration of each time interval according to the output value of the electronic memory of evaluation electronics (23).

Figure 2:
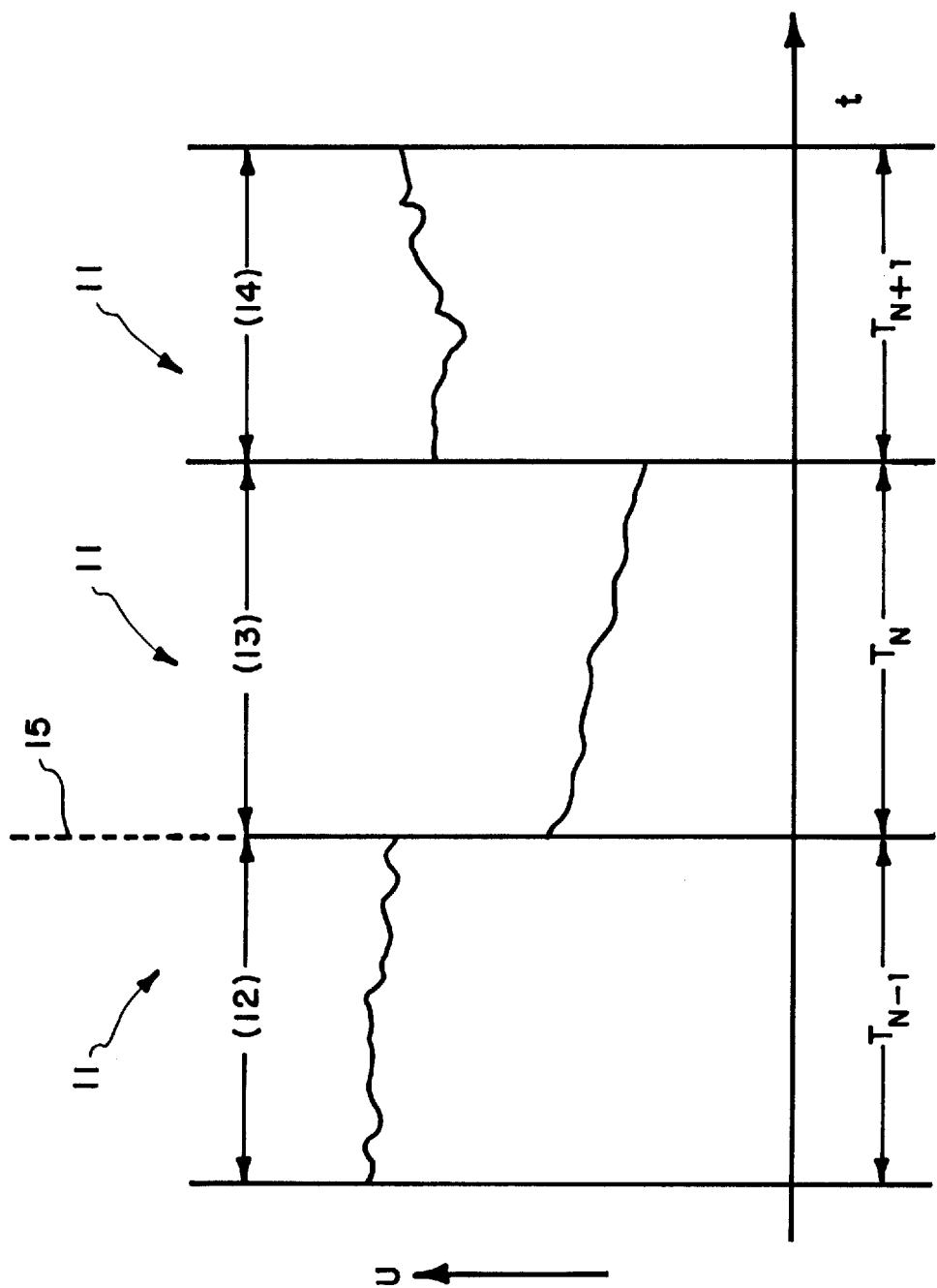

In FIG. 2 is shown, by way of illustration, the generator output voltage during three time intervals (11). The following time interval (13) with its duration of $T_N$, to which the elucidations refer, is restricted by the preceding time interval (12) with its duration of $T_{N-1}$ and the time interval after next (14) with the duration of $T_{N+1}$. The point in time (15) is at the border between the preceding and the momentary time interval.

Figure 3:
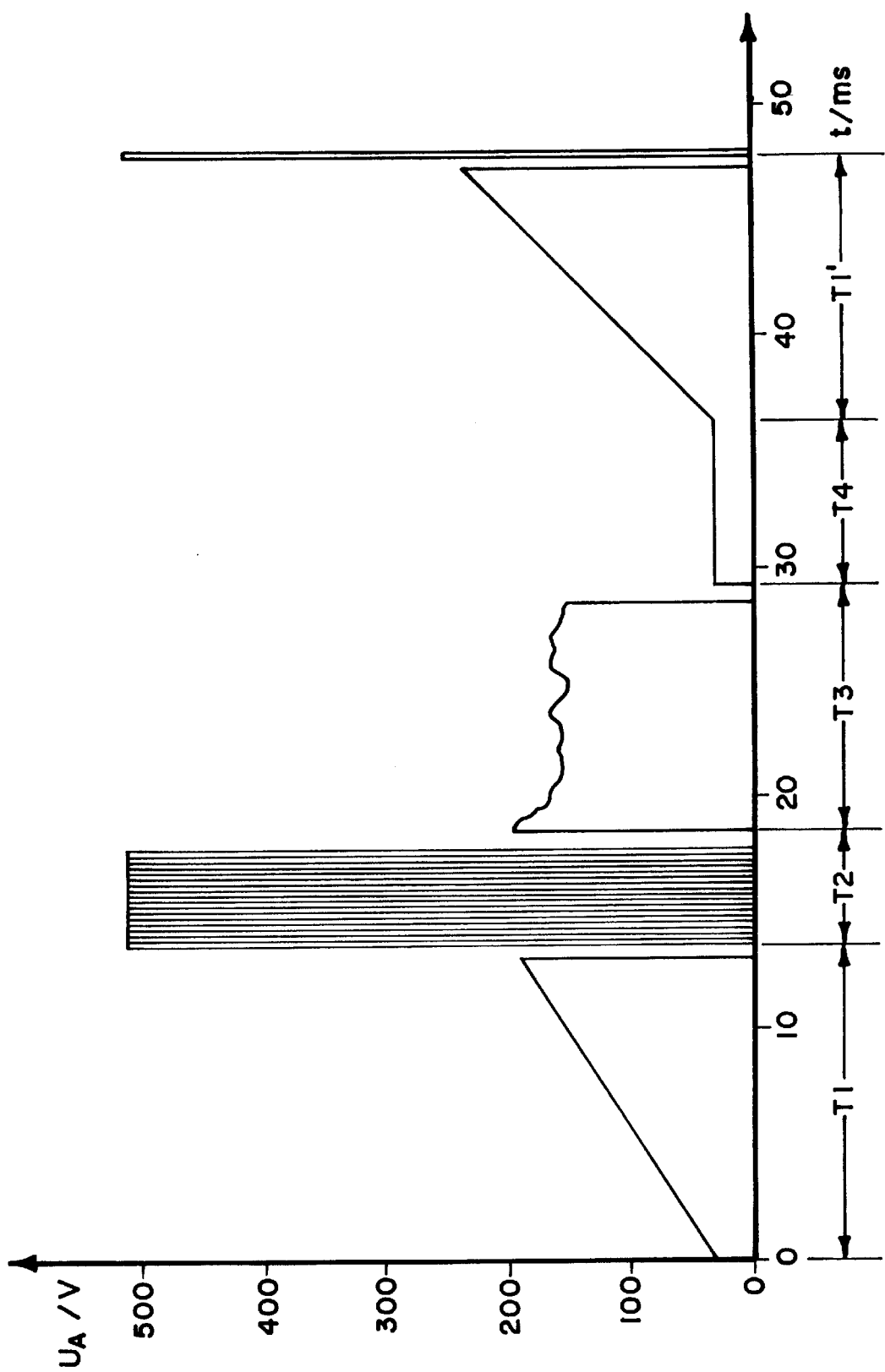

FIG. 3 shows, by way of illustration, the generator output voltage for a typical polypectomy application, in which sufficient coagulation must always be assured. During the interval T1, the generator voltage follows a rising flank. The generator voltage is relatively low compared to the following intervals. During this time, the tissue boils and thus coagulates. The current distribution in the tissue in the immediate vicinity of the cutting electrode corresponds approximately to a cylindrical field in which the greatest deep action can be attained. The time interval T1 ends automatically if measurement device (7) for determining the state of the tissue detects an electric arc between the cutting electrode and the tissue. Now time interval T2 follows in which short voltage impulses of a high amplitude are transmitted to the tissue. An electric arc always occurs with these voltage impulses. The pulses, however, are selected so short that the resulting cutting action is negligible. In this way, the surface is sealed during time interval T2. The flow field of the electric current in the tissue is spherical symmetrical starting from the arcing-over point of the spark. The deep action of the coagulation is relatively small. Following a preset time, this coaguluation interval is terminated. Next follows an interval with T3 in which the tissue is cut. In the illustrated example, the incision occurs with an adjustment of the size and intensity of the electric arc appearing when cutting. The duration of interval T3 depends on how long T1 lasted. Measurements show that if T1 lasts long, T3 can also last long without further cutting during coagulation. This is followed by interval T4 during which the generator only releases little output voltage. This little voltage is used to measure the tissue impedance. As long as the tissue impedance is high impedance, there is still an insulating vapor layer between the cutting electrode and the tissue. The tissue has to be cooled until this vapor layer has condensed and there is a direct ohmic contact between the cutting electrode and the tissue. The duration is determined via evolution device (3) for determining the tissue impedance at the cutting electrode contained in tissue state measurement device (7). This is followed by interval T1', again a phase for deep coagulation having a rising voltage ramp in voltage. Measurements show that advantageous cutting and coagulating properties can be obtained if all the intervals for deep coagulation are approximately the same length during tissue separation. For this reason, the steepness of the flank is regulated according to the time of the last interval required for deep coagulation. If the duration T1 was longer than desired, the rise of the ramp is selected steeper, as drawn, than in interval T1.

If the duration is too short, the ramp of the next interval for deep coagulation is set correspondingly flatter. Incisions having an output signal showed definite stoppage of the bleeding. An even incision was the result independent of the force exerted on the cutting electrode.

Figure 4:
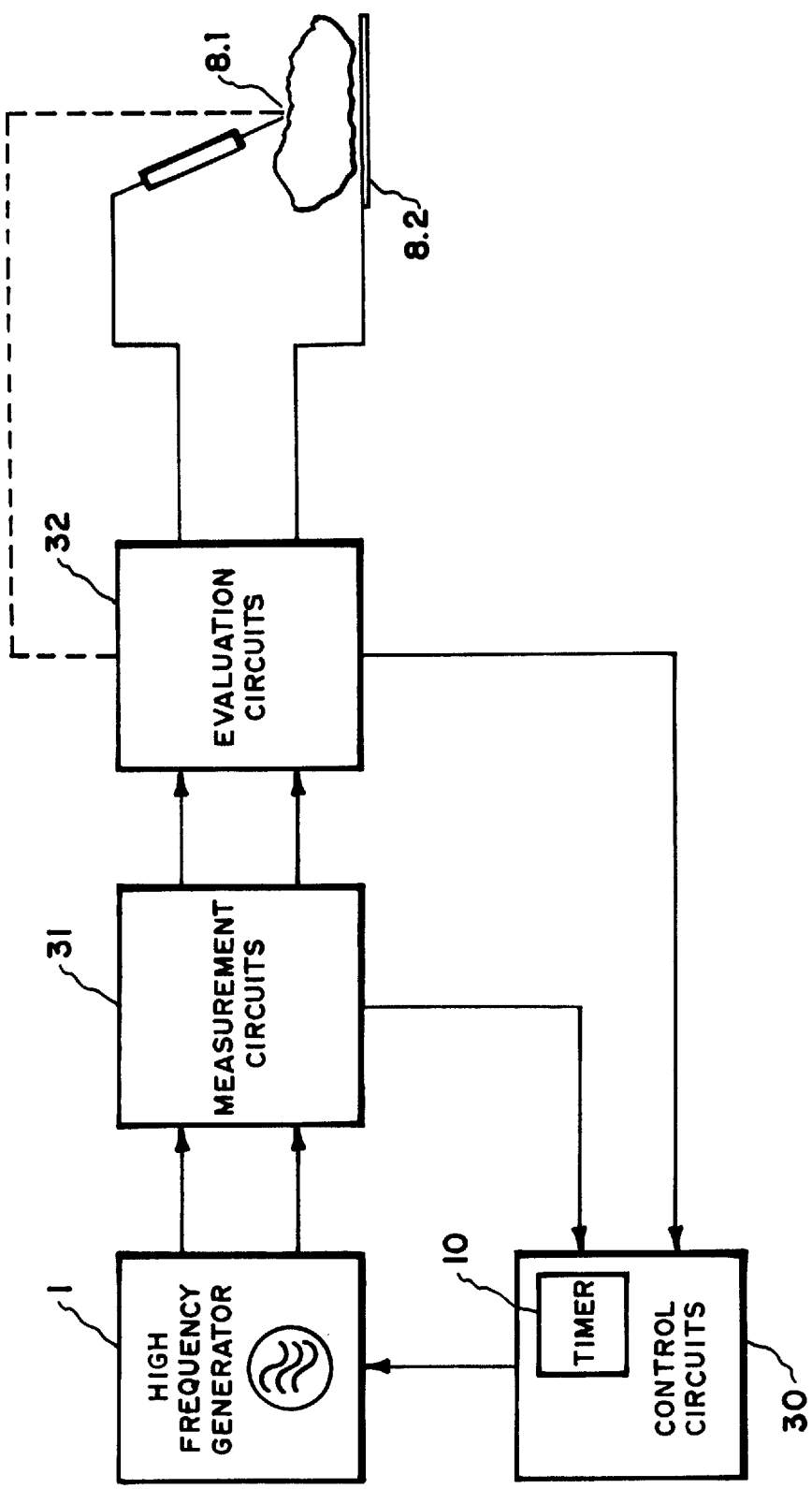

FIG. 4 shows the basic diagram of the major functions of the high-frequency surgery generator for carrying out safe high-frequency coagulation. The high-frequency generator (1) for high-frequency surgery having an adjustable output power supplies a high-frequency current to the tissue via a probe (8.1). The current flows back to the generator via another electrode (8.2). The electrode arrangement may be monopolar or bipolar. The monopolar arrangement consists of a small-surface probe (8.1) which is utilized at the operation site and a large-surface probe (8.2) which is disposed at some other part of the body of the patient. In the bipolar arrangement, the probe (8.1) and the electrode (8.2) have the same size surfaces and both are applied at the operation site having the same surface. With the aid of a control unit (30), at least one first mode of operation (a) having a coagulating function and a second mode of operation (b) having a cutting function are achieved. Timer (10) in control unit (30) limits the duration for the second mode of operation (b). Measurement device (31) having an evaluation unit conducts measurements of the electric parameters at the output of the generator during the time interval having the first mode of operation (a). Timer (10) is preset for the second mode of operation with the aid of the measured results. Evaluation circuit (32) which measures probe operations such as tissue impedance, mechanical position, arc harmonics and intensity is employed for the direct and/or indirect determination of the cutting, transmitting during the second mode of operation (b) a signal to the high frequency control unit (30) when the probe (8.1) commences cutting.

What is claimed is:

1. A high frequency surgical generating system for adjusting coagulation and cutting times and set momentary electrical outputs in which measurement means determines the state of tissue at a cutting probe comprising;

rising voltage applying means for applying a rising voltage to said cutting probe for a first interval of time to achieve deep coagulation;

detecting means detecting tissue state at the tissue to be cut when said rising voltage is applied, said detecting means terminating said first deep coagulating time interval at predetermined time by detecting condition at the tissue;

voltage applying means for applying short voltage impulses of high amplitude for a second interval of time to seal the surface of said tissue;

cutting voltage applying means for applying a cutting voltage to said tissue for a third time interval, said third time interval being determined from and set approximately equal to said first time interval;

measuring means measuring the condition of said tissue during said third time interval;

adjusting means adjusting said first time interval to achieve deep coagulation according to the condition of the tissue measured by said measuring means during said third time interval;

whereby said first deep coagulation time interval and said third cutting time interval are continuously adjusted according to the conditions measured at the tissue.

2. The system according to claim 1 in which said detecting means terminates said first deep coagulation time interval when an arc is detected.

3. The system according to claim 2 in which said measuring means measures the impedance at the tissue and adjusts said first deep coagulation time interval according to the impedance detected.

4. The system according to claim 3 in which said measuring means comprises; means applying a voltage to said tissue; and means measuring the voltage across said tissue to determine the impedance.

5. The system according to claim 4 in which said measuring means restarts said means for applying a rising voltage when said voltage measuring means detects a drop in impedance at said tissue and said tissue becomes conductive.

6. The system according to claim 5 in which said adjusting means increases said first deep coagulation time interval when said first time interval is too short and decreases said first deep coagulation time interval when said first time interval is too long.

7. The system according to claim 6 in which said adjusting means increases or decreases said first time interval by increasing or decreasing the rising rate of said rising voltage.

8. The system according to claim 7 in which said adjusting means adjusts the next operation of said first deep coagulation time interval and said third cutting time interval according to the condition of the tissue during the preceding deep coagulation and cutting time intervals.

9. The system according to claim 3 in which said adjusting means adjusts the next operation of said first deep coagulation time interval and said third cutting time interval according to the condition of the tissue during the preceding deep coagulation and cutting time intervals.

10. A method of controlling the operation for a high frequency surgical generating system for adjusting coagulation and cutting times and set momentary electrical outputs at a cutting probe comprising;

applying a rising voltage to a cutting probe in contact with tissue for a first interval of time to achieve deep coagulation;

detecting the condition of tissue to be cut when said rising voltage is applied;

applying short voltage impulses of high amplitude for a second interval of time to seal the surface of said tissue;

applying a cutting voltage to said tissue for a third interval of time approximately equal to the first interval of time for applying a rising voltage to cut said tissue and achieve deep coagulation;

measuring the condition at the tissue during said third interval of time;

adjusting said first interval of time for applying a voltage to achieve deep coagulation according to the condition at the tissue during said measuring;

whereby deep coagulation time interval and third cutting time interval are continuously adjusted according to conditions measured at the tissue during the deep coagulation time and are kept approximately equal.

11. The method according to claim 10 terminating said rising voltage when an arc is detected.

12. The method according to claim 11 in which said step of measuring the condition at the tissue measures the impedance at the tissue being cut; said adjustment of said first interval comprising adjusting the length of said first interval according to the impedance at said tissue.

13. The method according to claim 12 in which said first interval of deep coagulation begins when the impedance at said tissue drops to a conductive level.

14. The method according to claim 13 in which said adjustment of said first interval comprises adjusting the rising voltage to be greater when said first deep coagulation interval is too long and adjusting the rising voltage of said first interval to be lower when said first deep coagulation interval is too short.

15. The method according to claim 14 in which said adjustment of said first interval comprises adjusting the next operation of said first deep coagulation interval according to the condition of the tissue measured during the preceding deep coagulation and cutting operations.

16. The method according to claim 13 in which said adjustment of said first interval comprises adjusting the next operation of said first deep coagulation interval according to the condition of the tissue measured during the preceding deep coagulation and cutting operations.

* * * * *